(12) United States Patent
Biedenbach et al.

(10) Patent No.: US 6,310,214 B1
(45) Date of Patent: Oct. 30, 2001

(54) PROCESS FOR THE PREPARATION OF CHLOROPYRIDINE SULPHONIC ACID CHLORIDES

(75) Inventors: Bruno Biedenbach, Worms; Hans-Peter Michel, Buerstadt, both of (DE)

(73) Assignee: Ruetgers Organics GmbH, Mannheim (DE)

( * ) Notice: Subject to any disclaimer, the term of this patent is extended or adjusted under 35 U.S.C. 154(b) by 0 days.

(21) Appl. No.: 09/553,475

(22) Filed: Apr. 20, 2000

(30) Foreign Application Priority Data

Apr. 21, 1999 (DE) .............................. 199 18 021

(51) Int. Cl.$^7$ ...................... C07D 213/71; C07D 213/61
(52) U.S. Cl. ...................... 546/295; 546/318; 546/326
(58) Field of Search ................................. 546/295

(56) References Cited

U.S. PATENT DOCUMENTS

| | | | |
|---|---|---|---|
| 3,561,005 | 2/1971 | Somlo | 544/334 |
| 4,167,525 | 9/1979 | Kataoka et al. | 562/855 |
| 5,459,138 | 10/1995 | Pirotte et al. | 514/222.8 |

FOREIGN PATENT DOCUMENTS

| | | |
|---|---|---|
| 1 795 361 | 3/1972 | (DE) . |
| 25 14 334 | 10/1975 | (DE) . |
| 28 31 777 | 2/1979 | (DE) . |
| 618 209 | 10/1994 | (EP) . |
| 1 420 406 | 12/1966 | (FR) . |

OTHER PUBLICATIONS

J. Delarge, "Chemistry and Pharmacological Properties of the Pyridine–3–sulfonylurea Derivative Torasemide," Arzneimitt–Forsch/Drug Res. 38 (1), 1988, pp. 144–150.

P. de Tullio et al., "Synthesis and Structural Studies of a New Class of Heterocyclic Compounds: 1,2,4–Pyridothiadiazine 1,1–Dioxides, Pyridyl Analogues of 1,2,4–Benzothiadiazine 1,1–Dioxides", Tetrahedron, vol. 51 No. 11, 1995, pp. 3221–3234.

L. Thunus, "Synthèse de quelques dérivés pipérazinyl$_4$ pyridine substitutés en $_3$", Annales. Pharm. Française 33, No. 10, 1975, pp. 487–494.

Primary Examiner—Alan L. Rotman
(74) Attorney, Agent, or Firm—Foley & Lardner

(57) ABSTRACT

A process is disclosed for preparing chlorinated pyridine-sulphonic acid chlorides of the general formula I

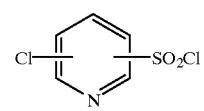

(I)

from hydroxypyridine-sulphonic acids of the general formula II

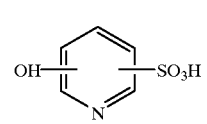

(II)

The process generally entails a) passing chlorine gas into a mixture of a hydroxypyridine-sulphonic acid and of phosphorus trichloride; b) heating the mixture of a) to temperatures of about 100 to about 120° C.; c) removing any phosphorus oxychloride formed and any excess phosphorus trichloride by distillation; d) taking up the residue with an organic solvent; and e) distilling the liquid phase in a vacuum, thereby obtaining the chlorinated pyridine-sulphonic acid chloride.

7 Claims, No Drawings

PROCESS FOR THE PREPARATION OF CHLOROPYRIDINE SULPHONIC ACID CHLORIDES

BACKGROUND OF THE INVENTION

The present invention is concerned with a new process for the preparation of chloropyridine sulphonic acid chlorides.

Chloropyridine sulphonic acid chlorides serve as starting materials for the preparation of a series of pharmaceuticals with anti-inflammatory, anti-pyretic, cardiovascular, blood sugar-sinking and diuretic properties. Thus, for example, 4-chloropyridine-3-sulphonamide serves for the preparation of torasemide and thus of related blood sugar-sinking sulphonylureas which also inhibit inflammation and act diuretically (see J. Delarge Arzneimitt.-Forsch./Drug Res., 38(1), 1988, 144). The sulphonarnide is, in turn, prepared from 4-chloro-pyridine-3-sulphonic acid chloride.

In DE 25 14 334 A1 is described a process for the preparation of chlorinated pyridine-3-sulphonic acid derivatives, whereby, starting from 4-pyridinol-3-sulphonic acid chlorides, there first takes place the chlorination by means of a mixture of $PCl_5$ and $POCl_3$. The excess $POCl_3$ and $PCl_5$ is stripped off in a vacuum, and the remaining residue is worked up in a complicated way in several steps. Similar processes with the use of $PCl_5/POCl_3$ are known from the literature (see L. Thunus, Annales pharmaceutiques francais, 33, 1975, 487; Tullio et al., Tetrahedron, 51, 1995, 3221, as well as EP 0 618 209 A1, DE 25 14 334 and FR 88,352).

The chlorination thereby takes place in one step by the substitution of the OH group on the ring and in the sulphonic acid residue with formation of hydrogen chloride and $POCl_3$. As halogenation agent, there serves exclusively phosphorus pentachloride, always used in excess, whereas phosphorus oxychloride is used as solvent since it is always obtained in the reaction mixture in the case of the reaction of the phosphorus pentachloride. Phosphorus oxychloride does not itself lead to the chlorination. After the reaction, it can be removed from the mixture by distillation and, without further purification steps, can be used again for the next batch.

Other chlorination agents, for example thionyl chloride, sulphuryl chloride or also phosphorus tri-chloride, essentially only replace the phenolic OH group and are, therefore, not suitable for the reaction.

It is a disadvantage of the known processes that, in the case of batches of large-scale size, the starting materials cannot be mixed together from the beginning, since this can lead to a longer controllable course of the reaction with a vigorous evolution of gas. Therefore, according to the prior art, there takes place a slow, measured addition of the acid to the boiling mixture of phosphorus pentachloride and phosphorus oxychloride, as well as possibly an after-dosing of $PCl_5$.

However, the dosing in of the solid reactants present in solid state (hydroxypyridine-sulphonic acid and $PCl_5$) leads to considerable problems. There are several possibilities for the addition. Either the reactors must be opened, whereby the aggressive chemicals HCl and $POCl_3$ are liberated, or the addition takes place with the help of transport means for solid materials, for example transport screws. In this case, too, problems arise since the contact of the solid substances with the boiling $POCl_3$ leads to no longer transportable adhesions and encrustations.

Since phosphorus pentachloride is always used in excess, unreacted $PCl_5$ sub-limes in the case of the distilling off of the solvent ($POCl_3$) and leads to encrustations and stoppages of the cooler. Furthermore, additional reaction steps for the decomposition of the excess halogenation agent by hydrolysis on ice, possible neutralisation with alkali and subsequent extraction are necessary. The yields of the known processes lie at about 70%.

SUMMARY OF THE INVENTION

Therefore, it is an object of the present invention to provide a process that overcomes the disadvantages of the prior art.

It is another object of the present invention to provide a process with which chlorinated pyridine-sulphonic acid derivatives can be prepared technically simply and in high yield.

In accomplishing these objects, there has been provided according to the present invention a process for preparing chlorinated pyridinesulphonic acid chlorides of the general formula I

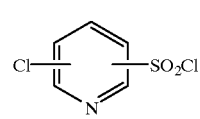

(I)

from hydroxypyridine-sulphonic acids of the general formula II

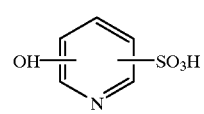

(II)

comprising
a) passing chlorine gas into a mixture of a hydroxypyridine-sulphonic acid and of phosphorus trichloride,;
b) heating the mixture of a) to temperatures of about 100 to about 120° C.;
c) removing any phosphorus oxychloride formed and any excess phosphorus trichloride by distillation;
d) taking up the residue with an organic solvent;
e) distilling the liquid phase in a vacuum, thereby obtaining the chlorinated pyridine-sulphonic acid chloride.

Further objects, features and advantages of the present invention will become apparent from the detailed description of preferred embodiments that follows.

DETAILED DESCRIPTION OF THE PREFERRED EMBODIMENTS

The present invention concerns a new process for the preparation of chloropyridine-sulphonic acid chlorides of the general formula I

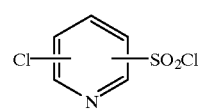

(I)

from hydroxypyridine-sulphonic acids of the general formula II

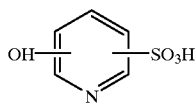

(II)

by substitution of the ring OH group and of the OH group of the acid residue by a chlorination agent, whereby, as chlorination agent, there is used a mixture of phosphorus trichloride in excess up to the stoichiometric amount and chlorine gas in stoichiometric amount up to a small insufficiency referred to the hydroxy pyridine-sulphonic acid used and whereby chlorine gas is passed into a mixture of hydroxypyridine-sulphonic acid and of phosphorus trichloride at temperatures of 100 to 120° C., the phosphorus oxychloride formed and possibly excess phosphorus trichloride are removed distillatively, the residue is taken up with an organic solvent and the liquid phase distilled in a vacuum for obtaining the chlorinated pyridine-sulphonic acid chloride.

The present invention addresses the deficiencies of the art in that chlorination of hydroxypyridine-sulphonic acids can be carried out with the help of a phosphorus trichloride-chlorine mixture known from carboxylic acid chemistry (see, inter alia, DE-OS 1 795 361, DE 28 31 777 A1), whereby, according to the present invention, a) into a mixture of hydroxypyridine-sulphonic acid and of phosphorus trichloride, chlorine gas is passed in at temperatures of 70 to 90° C. and whereby phosphorus trichloride is used in excess up to the stoichiometric amount and chlorine gas in stoichiometric amount up to a slightly insufficient amount referred to the hydroxypyridine-sulphonic acid;

b) subsequently heating to temperatures of 100 to 120° C.;

c) the phosphorus oxychloride formed and possibly the excess phosphorus trichloride removed by distillation;

d) the residue is taken up in an organic solvent;

e) the liquid phase is distilled in a vacuum for obtaining the chlorinated pyridine-sulphonic acid chloride.

For this purpose, the liquid phosphorus trichloride and the acid are taken and the mixture heated under reflux. Subsequently, chlorine is passed into the reaction mixture with heating, whereby there takes place not only a substitution of the phenolic OH group but also of the hydroxyl group in the acid residue. Surprisingly, no nuclear chlorination of the pyridine thereby takes place by the chlorine used but rather exclusively the exchange of the hydroxyl groups.

Post-reaction is allowed to take place in known manner and phosphorus oxychloride and possibly excess $PCl_3$ distilled off. The residue is taken up with a preferably halogen-free solvent, for example toluene or methyl tert-butyl ether (MTBE) and possibly filtered. In the same way, there can also be used balogenated solvents, for example methylene chloride, ethylene chloride or also chloroform. However, from environmental points of view, the use of halogen-free solvents is preferred.

Due to the stoichiometric or insufficient use of chlorine, almost no unreacted chlorination agent remains in the reaction mixture. Thus, the sulphonic acid chloride can be obtained directly distillatively from the residue taken up with the solvent in high yield of over 90% and with a high degree of purity of over 98% (HPLC).

In a preferred embodiment of the process according to the present invention, for the further increase of the degree of purity of the product, the organic phase is stirred with water for the separation of $POCl_3$ possibly remaining behind, the aqueous phase is separated off and the solvent is stripped off in a vacuum.

It has been shown that phosphorus trichloride can be used not only in excess but also stoichiometric amount relative to the hydroxypyridine-sulphonic acid, preferably, for the minimisation of the material requirement, the presence of an about 0.12 to about 2 fold excess relative to the hydroxypyridine-sulphonic acid is used. If $PCl_3$ is used as sole solvent an excess of up to 5 fold should be added to provide the necessary stirrability. According to the invention, the chlorine generally is used in equimolar amounts or a slight insufficiency. Preferably, working is carried out with an about 0.02 to about 0.05 mol % chlorine insufficiency. In this case, no unused chlorination agent remains in the reaction mixture, whereby the working up of the batch after thee separation of $POCl_3$ and $PCl_3$ is considerably simplified by the possibility of the directly obtaining the pyridine-sulphonic acid chloride by distillation from the reaction mixture taken up with the organic solvent.

The reaction takes place in a mixture of phosphorus trichloride and the acid, whereby, in the course of the reaction, phosphorus oxychloride is formed which serves as additional solvent. Advantageously, however, an addition of phosphorus oxychloride to the reaction mixture can take place for the initial improvement of the solubility. Typically, these amounts fie in the range of about 0.5 to about 5 mol, referred to about 1 mol of acid used.

As starting material for the process according to the invention, there can serve any desired hydroxypyridine-3-sulphonic acids. Preferably, however, hydroxypyridine-3-sulphonic acids, especially 4-hydroxypyridine-3-sulphonic acid, are used.

The chlorinated pyridine-sulphonic acid chloride is obtained in almost quantitative yield.

With the process according to the invention, by the use of liquid phosphorus trichloride and gaseous chlorine, there is given a substantially simplified carrying out of the process in comparison with the use of the solid and aggressive $PCl_5$. The course of the reaction can be controlled very simply via the amount and speed of introduction of the chlorine gas.

The organic phase obtained after the process according to the invention, which contains the chlorinated pyridinesulphonic acid chloride, can be used advantageously, without isolation of the sulphonic acid chloride, for the preparation of chlorinated pyridine sulphonamides. For this purpose, the organic phase is, after the washing step, mixed while stirring with aqueous ammonia. The pH value of the mixture is thereby to lie in the neutral to weakly basic range of about 7 to about 9.5.

Since the solubility of the product increases in the basic region and losses of yield can thereby arise, after ending of the reaction, in which a slight excess of ammonia is present, the pH value of the solution is possibly adjusted to about 7 to about 9.5 with acid, such as hydro-chloric acid or acidic salts.

For obtaining other acid amides, aqueous solutions of the appropriate amines can be used.

After the reaction, the product, which is sparingly soluble in the aqueous and organic phase, is filtered off, washed chloride-free with water and subsequently again washed with organic solvent. The drying of the amide formed takes place at temperatures of below about 50° C., preferably at ambient temperature, since the product is thermolabile, especially in a moist state. The product is obtained with a yield of about 77 to about 85%.

The following Examples are given for the purpose of illustrating the present invention:

EXAMPLE 1

Comparative Example with $Cl_2$ Excess

4-Chloropyridine-3-sulphonic acid chloride and 4-chloropyridine-3-sulphonamide

There are taken 1137.5 g (6.49 mol) 4-hydroxy-pyridine-3-sulphonic acid, 3481 g (2085 ml/22.7 mol) phosphorus oxychloride and 2115 g (1345 ml/15.4 mol) phosphorus trichloride and heated to reflux with stirring, whereby the sump temperature increases to about 80° C. In about 3 hours, 1092 g (15.4 mol) chlorine gas are passed into the reaction mixture which is immediately taken up by the mixture. With HCl evolution, the sump temperature increases to about 100° C. After 24 hours under reflux, whereby the sump temperature increases to 110° C. into the boiling range of the phosphorus oxychloride, the mixture becomes almost clear. 5550 g (3313 ml) phosphorus oxychloride are distilled off under water pump vacuum and can be reused. The residue is taken up at about 40° C. with 5030 g (4000 ml) ethylene chloride and, with external water cooling, mixed portionwise with 2600 ml water at a maximum of 30° C. After separation of the phases, the organic phase is stirred up twice with, in each case, 2500 ml water. By distilling off of the solvent and drying in a vacuum, the 4-chloropyridine-3-sulphonic acid chloride can be isolated in practically quantitative yield.

Technically, however, for the preparation of the sulphonic acid amide, the solution is directly mixed portionwise, with further stirring and external cooling, with 1015 g (1120 ml) of a 25% aqueous solution of ammonia (14.93 mol.) The temperature is thereby not to exceed 30–35° C. The mixture is intensively further stirred for about 3 hours, whereby the pH value is to remain in the basic range. Subsequently, it is neutralized with about 195 g (165 ml/1.95 mol) concentrated hydrochloric acid and, after further stirring for 3 hours, filtered off. The residue is washed with 3250 ml water and subsequently with 2075 g (1650 ml) ethylene chloride and dried in the air at ambient temperature.

There are obtained about 1050 g (5.45 mol) 4-chloropyridine-3-sulphonamide in about 84% yield. The product has a melting point of 152° C. with decomposition and a chlorine content of 18.1 to 18.6%. The purity is 99% (HPLC).

As solvent, chloroform can also be used, whereby, in this case, because of the smaller solubility of the 4-chloropyridine-3-sulphonic acid chloride, double the volume of solvent is needed.

EXAMPLE 2

4-Chloropyridine-3-sulphonic acid chloride and 4-chloropyridine-3-sulphonamide

A mixture of 1137 g (6.40 mol) 4-hydroxypyridine-sulphonic acid, 3481 g (2085 ml/22.7 mol) phosphorus oxychloride and 2115 g (1345 ml/15.4 mol) phosphorus trichioride is heated to reflux with stirring, whereby the sump temperature increases to about 80° C. In about 3 hours, 920 g (12.98 mol) chlorine gas are passed into the reaction mixture which is immediately taken up by the mixture. With HCl evolution, the sump temperature increases to about 100° C. After stirring under reflux for 24 hours, whereby the sump temperature increases to 110° C. in the acid region of the phosphorus oxychioride, the mixture becomes almost clear. 5550 g (33.3 ml) phosphorus oxychloride are distilled off under water pump vacuum and can be used again. The residue is taken up at about 40° C. with 5030 g (4000 ml) ethylene chloride and mixed portionwise with 2600 ml water with external water cooling at a maximum of 30° C. After separation of the phases, the organic phase is stirred out twice with, in each case, 2500 ml water. By distilling off the solvent and drying in a vacuum, the 4-chloropyridirie-3-sulphonic acid chloride can be isolated in practically quantitative yield.

Technically, however, for the preparation of the sulphonic acid amide, the solution is mixed portionwise with further stirring and external cooling, with 1015 g (1120 ml/14.93 mol) 25% aqueous ammonia. The temperature is thereby not to exceed 30–35° C. It is intensively after-stirred for about 3 hours, whereby the pH value is to remain in the basic region. Subsequently, it is neutralised with about 195 g (165 mol/1.95 mol) concentrated hydrochloric acid and, after further stirring for 3 hours, filtered off. The residue is washed with 3250 ml water and subsequently with 2075 g (1650 ml) ethylene chloride and dried in the air at ambient temperature.

There are obtained about 1050 g (5.45 mol) 4-chloropyridine-3-sulphonamide in about 84% yield. The product has a melting point of 153° C. with decomposition. The purity is 99.6% (HPLC).

As solvent, chloroform can also be used, whereby, in this case, because of the lower solubility of the 4-chloropyridine-3-sulphonic acid chloride, double the volume of solvent is needed.

EXAMPLE 3

4-Chloropyridine-3-sulphonamnide 25 g (0.16 mol) phosphorus oxychloride are taken and mixed with 103 g (0.75 mol) phosphorus trichloride. With stirring, it is added to a solution of 56.3 g (0.32 mol) 4-hydroxypyridine-3-sulphonic acid and heated under reflux to about 80° C. 44.5 g (0.62 mol) chlorine are then passed in within 3 to 4 hours, whereby the reflux temperature increases to 103 to 108° C. After-reaction is allowed to take place for 20 hours, whereby the temperature increases to 105 to 110° C. and the yellowish solution becomes almost clear. It is then cooled to about 50° C. and phosphorus oxychloride and $PCl_3$ completely distilled off under vacuum. The distillation residue is mixed with 200 ml toluene, filtered off at 20 to 25° C. and the filter residue again washed with a little toluene. The organic phase is stirred out twice with, in each case, 100 ml water and the aqueous phase separated off. The toluene phase is mixed with 30 ml acetone and 52 to 55 ml (0.67–0.7 mol) of a 24% aqueous ammonia solution added dropwise at 20 to 25° C. with stirring within about 3 hours. Stirring is continued for a further 9 hours, whereby the pH value of the solution at the end of the reaction lies at about 9. The precipitated product is filtered off with suction and washed chloride-free 3 times with, in each case, 50 ml water and subsequently twice with, in each case, 50 ml toluene. The product is dried at ambient temperature. There are obtained 51.6 g (0.268 mol) 4-chloro-pyridine-3-sulphonamide with a melting point of 153° C. (decomposition), corresponding to a yield of about 84%. The purity is 99.7% HPLC).

The addition of acetone (preferably 15%, referred to the toluene used) is unimportant for the purity and yield. By the addition, on the one hand there is prevented an encrustation of the product on the walls of the reactor and, on the other hand, a better mixing up of the phases and therewith finally an acceleration of the reaction.

Instead of toluene, MTBE can also be used as solvent.

EXAMPLE 4

4-Chloropyridine-3-sulphonamide 137 g phosphorus trichloride are taken. While stirring, they are added to a solution of 56.3 g (0.32 mol) 4-hydroxypyridine-3-sulphonic acid and heated to reflux at about 77° C. 44.5 g (0.62 mol) chlorine are then passed in within 3 to 4 hours, whereby the reflux temperature gradually increases. While stirring, post-reaction is allowed for 20 hours, whereby the temperature increases to 105 to 110° C. and the yellowish solution becomes almost clear. It is then cooled to about 50° C. and phosphorus oxychloride and $PCl_3$ completely distilled off under vacuum. The distillation residue is mixed with 200 ml toluene, filtered at 20 to 25° C. and the filter residue again washed with a little toluene. The organic phase is stirred out twice with, in each case, 100 ml water and the aqueous phase separated off. The toluene phase is mixed with 30 ml acetone and 52 to 55 ml (0.67–0.7 mol) of a 24% aqueous ammonia solution added drop-wise at 20 to 25° C. with stirring within about 3 hours. It is further stirred for 9 hours, whereby the pH value of the solution at the end of the reaction lies at about 9. The precipitated product is filtered off with suction and washed chloride-free 3 times with, in each case, 50 ml water and subsequently washed twice with, in each case, 50 ml toluene. The product is dried at ambient temperature. There are obtained 51.1 g (0.265 mol) 4-chloropyridine-3-sulphonamide with a melting point of 153° C. (decomposition), corresponding to a yield of about 83%. The purity is 99.7% (HPLC).

The addition of acetone (preferably 15% referred to the toluene used) is unimportant for the purity and yield. Due to the addition, on the one hand the encrustation of the product is prevented and, on the other hand, a better mixing up of the phases and thus finally an acceleration of the reaction is achieved.

Instead of toluene, MTBE can also be used as solvent.

EXAMPLE 5

4-Chloropyridine-3-sulphonic acid chloride

As in Example 4 but there are taken 150 g (0.98 mol) phosphorus oxychloride, 618 g (4.5 mol) phosphorus trichloride and 336 g (1.92 mol) 4-hydroxypyridine-3-sulphonic acid, and 167 g (3.75 mol) chlorine are passed in insufficiency within 6 hours. After the addition of 120 ml toluene and stirring up twice with 300 ml water, the organic phase is separated off and the toluene is removed in a vacuum. The product is distilled over in a vacuum at a head temperature of 84 to 105° C. and 0.1 to 0.2 mm Hg. There are obtained 372 g (1.75 mol) 4-chloropyridine-3-sulphonic acid chloride, corresponding to a yield of 93.3% referred to the chlorine used and of 91.4% referred to the 4-hydroxypyridine-3-sulphonic acid taken.

The 4-chloropyridine-3-sulphonic acid chloride obtained has a melting point of 44° C. (colourless melt). The 1H-NMR spectrum ($CDCl_3$) shows the following structures: 7.70 (d, 1H), 8.80 (d, 1H) and 920 (s, 1H). The purity is 99.8% (HPLC).

The product can possibly also be distilled in a vacuum directly after distilling off of $PCl_3$ and $POCl_3$.

EXAMPLE 6

4-Chloropyridine-3-sulphonic acid chloride

As in Example 4 but there are taken 893 g (6.5 mol) phosphorus trichloride and 336 g (1.92 mol) 4-hydroxypyridine-3-sulphonic acid, and 267 g (3.75 mol) chlorine passed in in insufficiency within 6 hours. After the addition of 1200 ml toluene and stirring up twice with 300 ml water, the organic phase is separated off and the toluene removed in a vacuum. The product is distilled over in a vacuum at a head temperature of 84 to 105° C. and 0.1 to 0.2 mm Hg. There are obtained 366 g (1.72 mol) 4-chloropyridine-3-sulphonic acid chloride, corresponding to a yield of 91.8% referred to the chlorine used and of 90.0% referred to the 4-hydroxypyridine-3-sulphonic acid taken.

The 4-chloropyridine-3-sulphonic acid chloride obtained has a melting point of 44° C. (colourless melt). The $^1$H-NMR spectrum ($CDCl_3$) shows the following structures: 7.70 (d, 1H), 8.80 (d, 1H) and 9.20 (s, 1H). The purity is 99.8% (HPLC).

The product can possibly also be distilled in a vacuum directly after the distilling off of $PCl_3$ and $POCl_3$.

EXAMPLE 7

4-Chloropyridine-3-sulphonic acid chloride

As in Example 3 but 150 g (0.98 mol) phosphorus oxychloride, 6.18 g (4.5 mol) phosphorus trichloride and 336 g (1.92 mol) 4-hydroxypyridine-3-sulphonic acid are taken, and 267 g (3.75 mol) chlorine passed in in insufficiency within 6 hours. After the addition of 1200 ml toluene, the insoluble components are filtered off. The toluene and remaining phosphorus oxychloride are removed in a vacuum. The product is distilled over in a vacuum at a head temperature of 84 to 105° C. and 0.1 to 0.2 mm Hg. There are obtained 371 g (1.75 mol) 4-chloropyridine-3-sulphonic acid chloride, corresponding to a yield of 93.0% referred to the chlorine used and of 91.1% referred to the 4-hydroxypyridine-3-sulphonic acid taken.

The 4-chloropyridine-3-sulphonic acid chloride obtained has a melting point of 44° C. (colourless melt). The $^1$H-NMR spectrum ($CDCl_3$) shows the following structures: 7.70 (d, 1H), 8.80 (d, 1H) and 9.20 (s, 1H). The purity is 98.5% (HPLC).

German patent application DE 19918021.0, filed Apr. 21, 2000 is hereby incorporated by reference in its entirety.

We claim:

1. A process for preparing chlorinated pyridinesulphonic acid chlorides of the general formula I

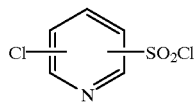

from hydroxypyridine-sulphonic acids of the general formula II

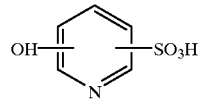

comprising
a) passing chlorine gas into a mixture of a hydroxypyridine-sulphonic acid and of phosphorus trichloride;
b) heating the mixture of a) to temperatures of about 100 to about 120° C.;
c) removing any phosphorus oxychloride formed and any excess phosphorus trichloride by distillation;
d) taking up the residue with an organic solvent; and
e) distilling the liquid phase in a vacuum, thereby obtaining the chlorinated pyridine-sulphonic acid chloride.

2. The process according to claim 1, wherein a) is accomplished using an excess, over the stoichiometric amount, of phosphorus trichloride and chlorine gas is used in a stoichiometric amount, or slightly less than a stoichiometric amount, with reference to the hydroxypyridine-sulphonic acid.

3. The process according to claim 2, wherein phosphorus trichloride is used in about 0.15 to about 0.2 fold excess and chlorine gas in an insufficiency of about 0.02 to about 0.05 mol %.

4. The process according to claim 3, wherein toluene, methyl tert-butyl ether, chloroform, methylene chloride or ethylene chloride is used as the organic solvent.

5. The process according to claim 4, wherein the phosphorus oxychloride is added to the reaction mixture prior to chlorination.

6. The process according to claim 5, wherein the hydroxypyridine sulphonic acid is 4-hydroxypyridine-3-sulphonic acid.

7. The process according to claim 6, wherein the residue in d) is stirred with water, the organic phase is evaporated, thereby obtaining the chloropyridine-sulphonic acid chloride, and the product is distilled under vacuum at about 0.1 to about 0.3 mm Hg and at a temperature of about 80 to about 115° C.

* * * * *